United States Patent [19]

Clinton et al.

[11] 4,133,640
[45] Jan. 9, 1979

[54] CHROMATOGRAPHIC ANALYSIS APPARATUS

[75] Inventors: Russell M. Clinton, Houston; A. Allilee Taylor, Mont Belvieu; Jimmy W. Brown, Dayton, all of Tex.

[73] Assignee: Gulf Oil Corporation, Pittsburgh, Pa.

[21] Appl. No.: 878,500

[22] Filed: Feb. 16, 1978

[51] Int. Cl.² ............... G01N 25/02; G01N 31/08
[52] U.S. Cl. .................. 23/230 PC; 23/230 M; 23/232 C; 73/23.1; 422/78
[58] Field of Search ....... 23/232 C, 230 PC, 253 PC, 23/230 M; 73/23.1

[56] References Cited

U.S. PATENT DOCUMENTS

| | | | |
|---|---|---|---|
| 3,425,807 | 2/1969 | Levy | 23/253 PC |
| 3,518,059 | 6/1970 | Levy | 23/253 PC |
| 3,847,546 | 11/1974 | Paul | 23/232 C |
| 3,847,554 | 11/1974 | Su | 23/230 M |
| 3,861,874 | 1/1975 | Krc | 23/230 PC |

*Primary Examiner*—R.E. Serwin
*Attorney, Agent, or Firm*—Richard L. Kelly

[57] ABSTRACT

Apparatus is provided for the chromatographic analysis of a plurality of samples having volatile components present in a nonvolatile matrix. The apparatus includes as its principal elements:

(a) an oven,
(b) A sample cylinder mounted in the oven, which cylinder includes an entry port external of the oven for admitting and withdrawing sample boats from the cylinder,
(c) A chromatographic analysis column mounted in the oven,
(d) A detector element for analyzing the outlet gas of the analysis column,
(e) Two chromatographic trap columns external of the oven,
(f) A first gas line for feeding a first carrier gas through the sample cylinder and one of the trap columns,
(g) A second gas line mounted in the oven for feeding a second inert carrier gas through one of the trap columns and the analysis column, and
(h) A valve assembly having two fixed operating positions which feed the two carrier gases in reversed flow through different trap columns when changed from one operating position to the other.

9 Claims, 9 Drawing Figures

CHROMATOGRAPHIC ANALYSIS APPARATUS

SUMMARY OF THE INVENTION

The apparatus of the invention includes as its principal elements:
(a) An oven,
(b) A sample cylinder mounted in the oven, which cylinder includes an entry port external of the oven for admitting and withdrawing sample boats from the cylinder,
(c) A chromatographic analysis column mounted in the oven,
(d) A detector element for analyzing the outlet gas of the analysis column,
(e) Two chromatographic trap columns external of the oven,
(f) A first gas line for feeding a first carrier gas through the sample cylinder and one of the trap columns,
(g) A second gas line mounted in the oven for feeding a second inert carrier gas through one of the trap columns and the analysis column, and
(h) A valve assembly having two fixed operating positions which feed the two carrier gases through different trap columns when changed from one operating position to the other and which reverse the direction of gas flow through the trap columns, The apparatus is designed to operate in two repetitive operating cycles. In the first cycle, the oven temperature is increased from a preselected lower temperature to a preselected higher temperature to volatilize volatile components from a sample and the first carrier gas stream carries these volatilized components through the valve assembly to one of the trap columns which is maintained at ambient temperature. Simultaneously, the second carrier gas stream is passed through the second trap column which is rapidly heated to volatilize the volatile components trapped therein in the immediately preceding operating cycle. These volatile components pass through the analysis column, which separates them into individual compounds, and then the detector which generates signals indicative of their chemical composition.

After completion of operations in the first cycle, the valve assembly is changed to its second operating position which reverses the carrier gas flow through different trap columns and also reverses the direction of the gas flow through each trap column. In the second operating cycle, all operating steps are carried out in the same manner as in the first cycle, except that the trap column maintained at ambient temperature in the first cycle is heated and the trap column heated in the first cycle is maintained at ambient temperature.

DETAILED DESCRIPTION OF THE INVENTION

Construction of Apparatus

Construction of Apparatus

Figure 1:
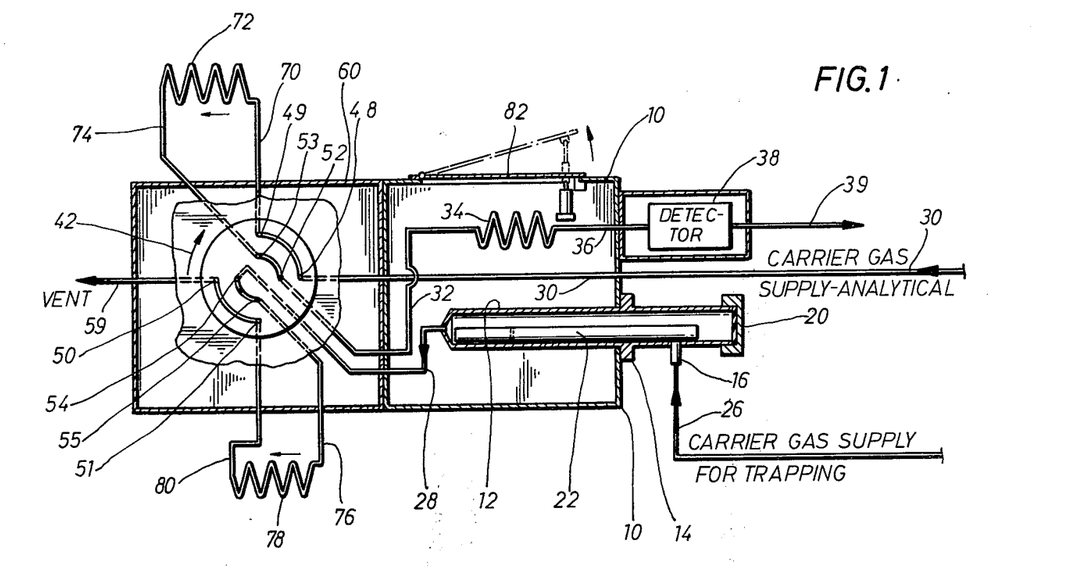
FIG. 1 is a sketch, partially in section, showing an operative assembly of elements in one embodiment of the invention.
Figure 2:
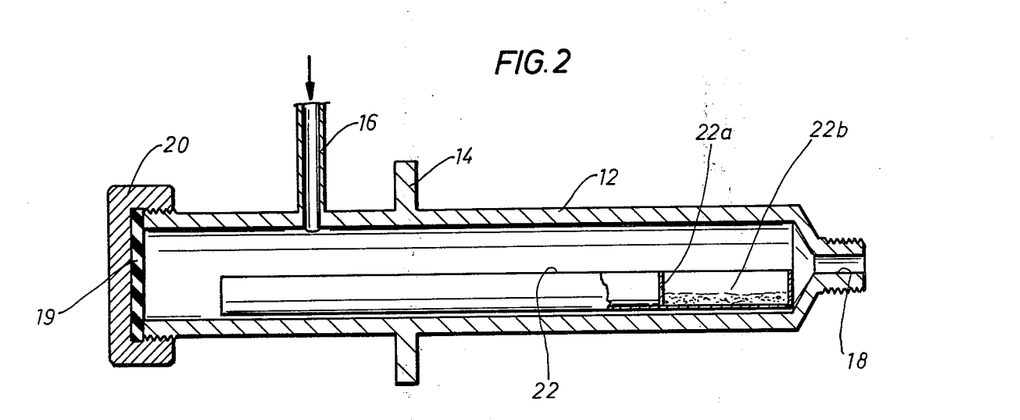
FIG. 2 is an enlarged view of the sample cylinder shown in FIG. 1.

The apparatus of FIG. 1 includes an oven 10. Suitable heating means (not shown) are provided to maintain the oven temperature at a preselected lower temperature, typically 100° C., and in response to a signal to increase the temperature to a preselected higher temperature, typically 300° C. A door 82 is provided in oven 10 which can be opened periodically to cool the oven. A cylinder 12, whose structure is shown in greater detail in FIG. 2, is mounted in oven 10. Cylinder 12 contains a flange 14 which abuts against the wall of oven 10, a gas inlet 16 and a gas outlet 18. The inlet end of the cylinder is threaded to accept a threaded nut 20 which contains a rubber septum 19. A sample boat 22 having a vertical dividing wall 22a is positioned within the cylinder. The wall 22a defines a section 22b which serves to hold the sample being analyzed. Gas line 26 is connected to inlet 16 and gas line 28 is connected to outlet 18. Line 28 also connects to inlet 54 of a rotatable valve assembly mounted in oven 60 and whose structure and operation will be described subsequently. A gas line 30 runs through oven 10 and connects to inlet 48 of the valve assembly. Another gas line 32 leading from outlet 52 of the valve assembly runs through oven 10 and connects to the inlet of a chromatographic analysis column 34. The packing in this column is a high boiling silicone oil supported on kieselguhr. Line 36 connects the outlet of column 34 to the inlet of a detector element 38. Detector 38 can be of any conventional type such as an ionization detector and is maintained in a fixed temperature oven 37 so that it operates under isothermal conditions. Line 39 vents the outlet of detector 38 to the atmosphere. The segments of lines 28 and 32 which run between oven 10 and oven 60 are heated to a temperature at least as high as the higher preselected temperature of oven 10.

Figure 3A:
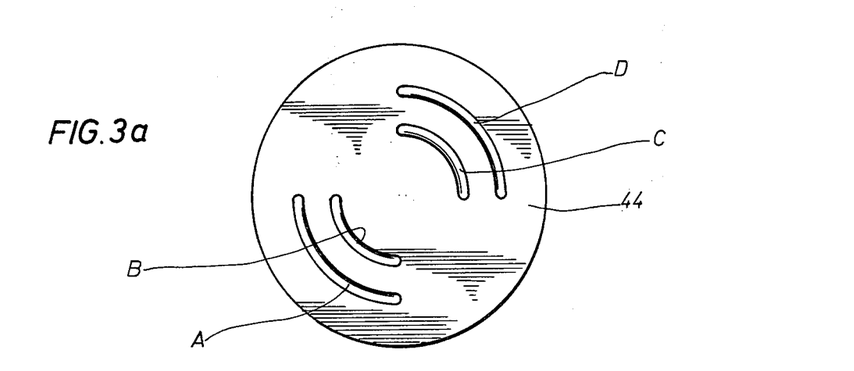
FIG. 3a is a bottom plan view of the rotatable top member of the valve assembly illustrated in FIG. 1.
Figure 3B:
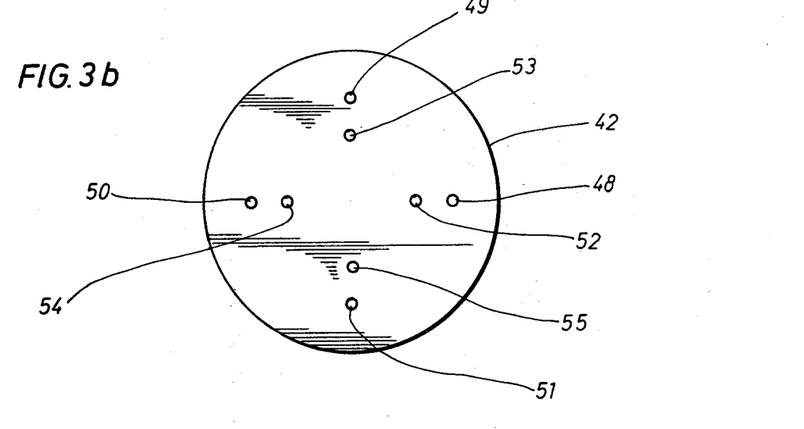
FIG. 3b is a top plan view of the fixed bottom member of the valve assembly illustrated in FIG. 1.

FIGS. 3a and 3b show the construction of the rotatable valve assembly. The assembly consists of a fixed bottom plate member 42 and a rotatable top plate member 44. Four orifices 48, 49, 50 and 51 are provided in plate member 42 and serve as inlets or outlets to the valve assembly. These orifices are equally spaced from each other and lie on the circumference of a circle drawn from the center point of plate member 42. Four additional orifices 52, 53, 54, and 55 are provided in plate member 42 and also serve as inlets or outlets to the valve assembly. These orifices also are equally spaced from each other and lie on the circumference of a circle drawn from the center point of plate member 42.

Rotatable top plate member 44 has four accurate grooves A, B, C, and D machined in its face. Each groove corresponds to an arc of 90° and lies on the circumference of a circle. The circles have the same radii as the circles whose circumferences include the orifices of fixed plate member 42. The touching faces of members 42 and 44 are fabricated from a high temperature resistant gasket material such as polytetrafluoroethylene (PTFE) to provide a gas tight seal between plate members 42 and 44. When the top plate member is rotated to the operating position shown in FIGS. 1 and 3a, groove A provides a gas passage between orifices 50 and 51; groove B provides a gas passage between orifices 54 and 55; groove C provides a gas passage between orifices 52 and 53; and groove D provides a gas passage between orifices 48 and 49. As shown in FIG. 1, the top member 44 is removed to shown orifices 48–52, inc., and the shaded arcs shown illustrate the gas passages between the orifices.

Figure 3C:
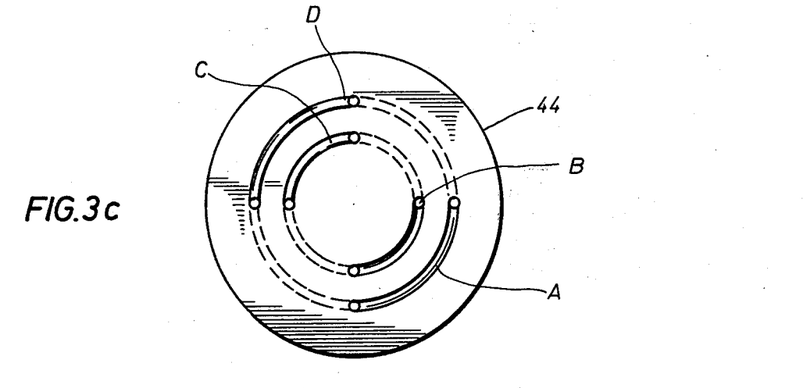
FIG. 3c is a view corresponding to FIG. 3a after the top member has been rotated through an arc of 90° to its second operating position.

The plate members 42 and 44 have suitable stops (not shown) so that plate member 44 can be readily rotated between the two positions shown in FIGS. 3a and 3c. When plate member 44 is rotated to the position illustrated in FIG. 3c, groove A provides a gas passage between orifices 48 and 51; groove B provides a gas passage between orifices 52 and 55; groove C provides a gas passage between orifices 53 and 54; and groove D provides a gas passage between orifices 49 and 50.

Figure 6:
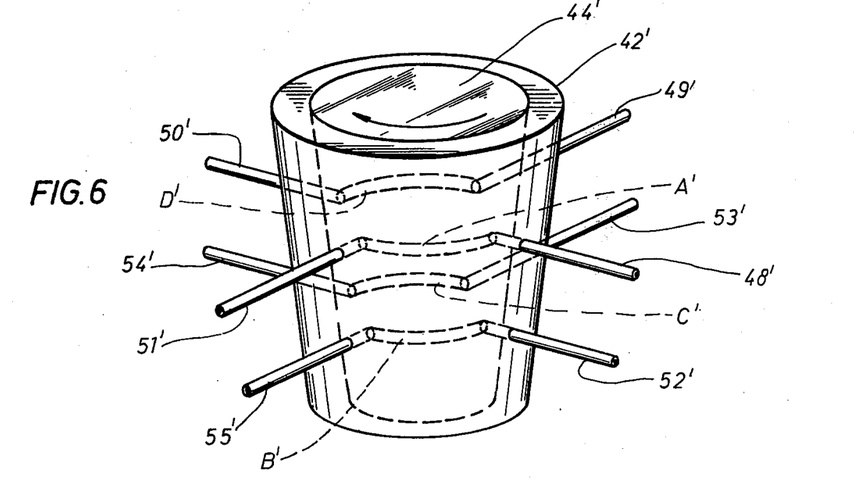
FIG. 6 is a perspective view of an alternate construction of a valve assembly that can be employed in the apparatus of FIG. 1.

FIG. 6 illustrates an alternate construction of a suitable valve assembly. In this construction the fixed member 42' has the shape of an inverted truncated cone whose center section is hollowed out. A first series of inlets or outlets 52', 53', 54', and 55' and a second series of inlets or outlets 48', 49', 50', and 51' are provided, with the inlet/outlets of each series being equidistant from each other and lying on the circumference of a circle lying in a plane passing through the inlets/outlets. The rotatable valve member 44' has the shape of an inverted truncated cone and fits into the opening of member 42'. A series of arcuate grooves A', B', C', and D' are provided and serve the same function as the grooves provided in plate member 42.

Referring again to FIG. 1, line 70 connects orifice 49 to the inlet of a first chromatographic trap column 72 and line 74 connects the outlet of column 72 to orifice 53. Line 76 connects orifice 55 to the inlet of a second chromatographic trap column 78 and line 80 connects the outlet of column 78 to orifice 51. Lines 74 and 76 and trap columns 72 and 78 are provided with heating means (not shown) so that they can be rapidly heated to at least the higher preselected temperature of oven 10. Typically, the heating means will heat these elements to a temperature of 350° C. within 2 minutes. Each of columns 72 and 78 is packed with a suitable absorbent medium which may be the same absorbent medium employed in analysis column 34.

Operation of Apparatus

Figure 4:
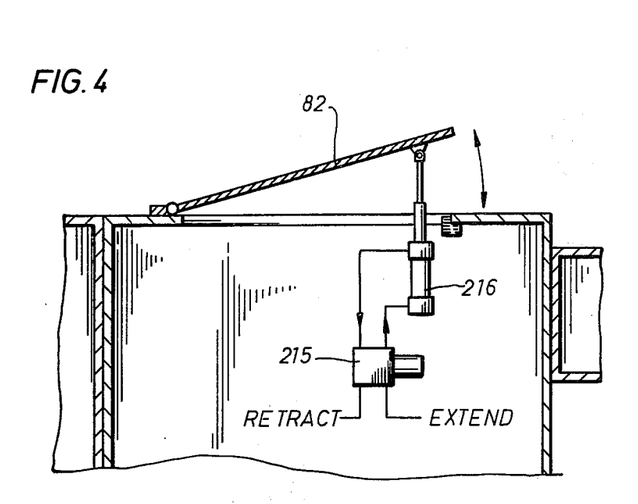
FIG. 4 illustrates a mechanism for opening and closing the door of the oven shown in FIG. 1.

The apparatus of the invention is designed to carry out a chromatographic analysis of the volatile components of a sample in two timed sequential steps. The apparatus also is designed to simultaneously carry out the first step of one analysis, while it is simultaneously carrying out the second step of the analysis of the immediately preceding sample. In the description of the operation of the apparatus, reference will be made to the circuit diagram of electrical controls illustrated in FIG. 5, and the apparatus of FIG. 4 which opens and closes door 82 of oven 10.

Figure 5:
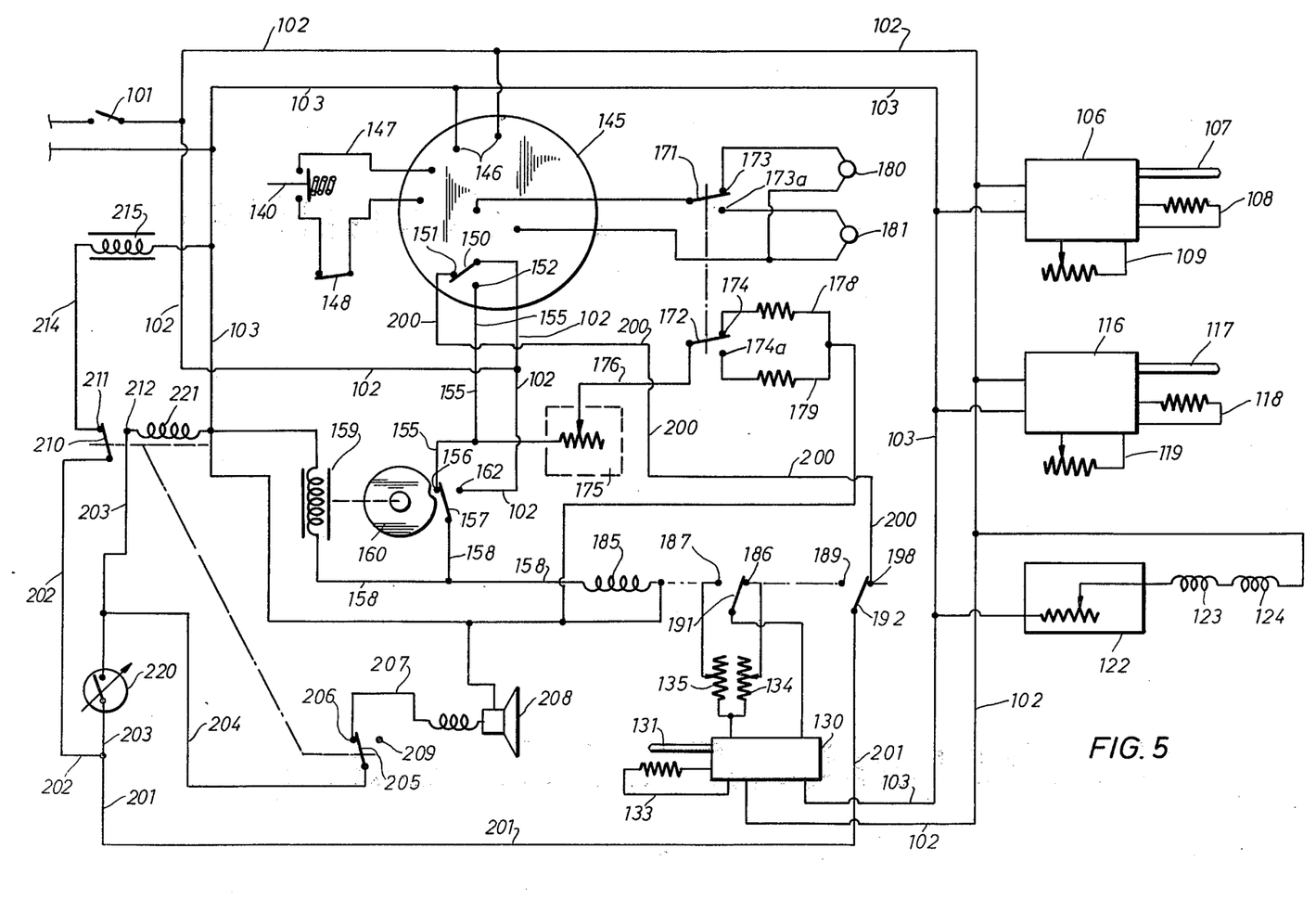
FIG. 5 is a circuit diagram of electrical controls for operation of the apparatus of FIG. 1.

The apparatus is activated by closing main switch 101 which provides power to the apparatus through lines 102 and 103. Power from lines 102 and 103 is fed to a first proportional temperature controller 106 which includes a thermocouple 107 and an electrical heating element 108, both of which are positioned in oven 37. The temperature in oven 37 is maintained at a preselected temperature, typically 350° C., by a set point potentiometer 109. Power from lines 102 and 103 also is fed to a second porportional temperature controller 116 which includes a thermocouple 117 and an electrical heating element 118, both of which are positioned in oven 60. The temperature in oven 60 is maintained at a preselected temperature, typically 350° C., by a second set point potentiometer 119. Lines 102 and 103 also feed power through a variable voltage controller 122 to two heating elements 123 and 124 which are connected in series and wrapped around, respectively, the segments of lines 28 and 32 which pass through the walls of ovens 10 and 60. The voltage is adjusted so that these segments of lines 28 and 32 are maintained at a temperature of about 350° C. Power from lines 102 and 103 also is fed to a third proportional temperature controller 130 which includes a thermocouple 131 and a heating element 132, both of which are positioned in oven 10. The temperature in oven 10 is controlled at a preselected temperature, typically 100° C., by means of set point potentiometer 134. Power from lines 102 and 103 also is fed to a contact pyrometer 145 through contact points 146.

After oven 10 has reached its lower set operating temperature, sealing nut 20 is removed and a sample boat 22 containing a weighed sample of polyethylene in section 22b is inserted into cylinder 12. Sealing nut 20 then is screwed onto cylinder 12 to seal the system. A carrier gas such as helium is fed continuously into cylinder 12 at a preselected rate, typically 40 ml/min. Valve plate 44 is set at the operating position shown in FIG. 3a so that the interconnections between the orifices of valve plate member 42 are shown in FIG. 1. A double pole, double throw switch containing poles 171 and 172 is set so that poles 171 and 172 assume the position shown in FIG. 5. The apparatus then is in a condition to begin its first cycle of operation.

Element 147 included in contact pyrometer 145 is an off at limit shorting device which includes a program starting button 140 which is normally closed. The first cycle is initiated by momentarily depressing program control button 140 which, through the internal wiring of contact pyrometer 145, activates switch 150 to move it from contact point 151 to contact point 152. Switch 150 will remain in this position until the preselected temperature limit set point of pyrometer 145 is reached. Power flows from line 102 through switch 150, line 155 contact point 156, switch 157, and line 158 to motor 159 which drives timing cam 160. As timing cam 160 begins it rotation, it thows switch 157 from contact point 156 to contact point 162. After switch 157 is positioned against contact point 162, power to drive motor 159 is supplied independently of contact pyrometer 145 by means of line 102, contact point 162, switch 157 and line 158. The movement of switch 150 to contact point 152 also causes a double pole, double throw relay 221 containing poles 205 and 210 to release to the position shown in FIG. 5.

The application of power to line 158 feeds power through an oven temperature relay 185 which consists of a double pole, double throw switch. The power closes relay 185 moving pole 191 from contact point 186 to contact point 187 and moving pole 192 from contact point 188 to contact point 189. The switching of pole 191 from contact point 186 to contact point 187 cuts set point potentiometer 134 out of the circuit heating oven 10 and cuts a second set point potentiometer 135 into the circuit. Set point potentiometer 135 is set to control oven 10 at a higher temperature, typically 300° C. Consequently, the proportional temperature controller 130 now permits the oven 10 to be heated to the higher preselected temperature. This oven temperature is maintained until timing cam 160 completes its cycle.

In the first cycle of operation of the apparatus, the carrier gas entering cylinder 12 flows through line 28, orifice 54, groove B, orifice 55, line 76, trap column 78, line 80, orifice 51, groove A, orifice 50, and line 59 which vents to the atmosphere. As the temperature in oven 10 is increased, volatile components present in the sample are vaporized and carried by the carrier gas through the lines previously described. The volatile components in the carrier gas are maintained in the gas phase by the elevated temperature maintained in line 28, valve members 42 and 44, and line 76. In this first cycle of the operation, trap column 78 is not heated and is maintained at ambient temperature. Upon entering column 78, the carrier gas is cooled and the volatile components originally present in the sample are condensed and absorbed upon the absorbent medium packed therein.

The flow of power from line 155 is fed through a variable voltage controller 175, line 176, and switch 172 to heating element 178. Element 178 heats trap column 72 and line 74. Controller 175 is set so that trap column 72 is rapidly heated, typically within 2 minutes, to a temperature of about 350° C. Thermocouple 180 is in contact with trap column 72 and feeds signals to contact pyrometer 145. Contact pyrometer 145 is set to deactivate switch 150 and move it from contact point 152 to contact point 151 when trap column 72 reaches its maximum desired temperature, typically 350° C. When switch 150 is in this position, no further power is fed to heating element 178.

While the first carrier gas entering cylinder 12 is passing through the apparatus as previously described, a second carrier gas such as helium is fed through a second gas circuit at a preselected rate, typically 30 ml/min. The second carrier gas passes through line 30, orifice 48, groove D, orifice 49, line 70, trap column 72, line 74, orifice 53, groove C, orifice 52, line 32, chromatographic analysis column 34, line 36, detector element 38, and line 39 which vents to the atmosphere. The rapid heating of trap column 72 as above described volatilizes any volatile materials absorbed in column 72, and such materials are carried through the second carrier gas circuit, including analysis column 34. In the first analysis of the day, the second carrier gas performs no function other than to sweep any volatiles from trap column 72. Its function in the subsequent operations will be described later.

All elements continue to function as previously described until timing cam 160 completes 360° of rotation. When this occurs, switch 157 is moved from contact point 162 to contact point 156. This action cuts the power to line 158 and motor 159 and stops the rotation of cam 160. The cutting of power to line 158 also cuts the power to relay 185. This action causes the double pole, double throw switch to open and moves pole 191 from contact point 187 to contact point 186 and pole 192 from contact point 189 to contact point 188. This action cuts set point potentiometer 135 from the circuit and brings set point potentiometer 134 into the circuit controlling the temperature of oven 10. The action of bringing switch 192 into contact with contact point 188, closes a circuit so that power from line 200 is fed through contact 188, switch 192 and line 201 which ultimately is split into lines 202 and 203. Line 200 in turn receives its power through line 102, switch 150, and contact point 151.

Power from line 202 is fed through switch 210, contact point 211, and line 214 to electric solenoid 215. Electric solenoid 215 actuates air solenoid 216 (See FIG. 4) which causes an applied air pressure to open oven door 82. The opening of oven door 82 causes oven 10 to cool rapidly.

When the temperature has fallen below a preselected temperature, typically 100° C., a close on fall of temperature switch 220 closes to complete the circuit in line 203. Current from line 203 flows through line 204, switch 205, contact point 206, and line 207 to actuate an audible alarm 208 which alerts the operator to the fact that the first cycle of the operation is essentially completed. Current from line 203 also passes through contact point 212 and a three-second delay relay 221. At the completion of the three-second delay, a double pole, double throw switch having poles 205 and 210 is thrown so that pole 205 is switched from contact point 206 to contact point 209 to silence alarm 208. The throwing of pole 210 from contact point 211 to contact point 212 cuts the power to electric solenoid 215 so that air solenoid 216 closes oven door 82. Since power is supplied to contact point 212 through switch 210, relay 221 will stay in its closed position until power to line 201 is cut, notwithstanding the fact that element 220 has been opened by the rise of the temperature in oven 10. At this point, the first cycle of operation is completed.

To begin the second cycle of operation, valve plate 44 is rotated to the position shown in FIG. 3c and the manual double pole, double throw switch is thrown to its second position so that pole 171 is in contact with contact point 173a, and pole 172 is in contact with contact point 174a. The sample boat from first cycle of operation is removed from the sample cylinder 12 and replaced with a new sample boat containing a fresh weighed sample.

Program control button 140 is depressed which activates switch 150 to move it from contact point 151 to contact point 152. This action cuts the flow of power to lines 201 and 202 so that relay 221 is opened and the double pole, double throw switch containing poles 205 and 210 is thrown so that poles 205 and 210 take positions shown in FIG. 5.

The electrical systems in the second cycle operate in the same manner as in the first cycle previously described, with the single exception that the power fed through variable voltage controller 175 is fed to heating element 179. Element 179 heats trap column 78 and line 76. Thermocouple 181 is in contact with trap column 78 and feeds signals to contact pyrometer 145 so that power to heating element 179 is cut off when trap column 78 reaches its maximum desired temperature, which is the same temperature setting employed with trap column 72 previously described.

By reason of the change made in the position of valve member 44, the carrier gas introduced into sample cylinder 12 now flows through line 28, orifice 54, groove C, orifice 53, line 74, trap column 72, line 70, orifice 49, groove D, orifice 50, and line 59 which vents to the atmosphere. As trap column 72 is maintained at ambient temperature during the second cycle, the carrier gas is cooled upon entering trap column 72 and the volatile components originally present in the sample are condensed and absorbed upon the absorbent medium packed therein. It will be noted that the direction of gas flow through trap column 72 during the second cycle of operation is reversed from the direction of gas flow during the first cycle of operation.

By reason of the change in the position of valve member 44, the second carrier gas stream flows through line 30, orifice 48, groove A, orifice 51, line 80, trap column 78, line 76, orifice 55, groove B, orifice 52, line 32, chromatographic analysis column 34, line 36, detector element 38, and line 39 which vents to the atmosphere. It will be noted that the direction of gas flow through trap column 78 during the second cycle of operation is reversed from the direction of gas flow during the first cycle of operation. Thus column 78 is back flushed. The rapid heating of trap column 78 as previously described volatilizes the volatile materials absorbed in column 78 in the first cycle of operation. The flow of the carrier gas sweeps these volatile components through the valve assembly and line 32. All of the volatile materials are maintained in the vapor phase in passing through the valve assembly and the segment of line 32 maintained in oven 60. This action results by reason of the high temperature prevailing in these elements. During the first few minutes of the second cycle of operation, the temperature in chromatographic analysis column 34 will be considerably lower than the temperature prevailing in trap column 78 and all of the elements positioned in oven 60. For this reason, the volatile components carried through line 32 by the carrier gas will be absorbed near the entrance of analysis column 34. As second cycle continues, however, the temperature in analysis column 34 will be increased and the volatile components originally deposited near the entrance of column 34 will begin to move through column 34. The more volatile components will move through column 34 at the fastest rate and ultimately all of the volatile components will be passed through analysis column 34 into detector 38 in the order of their relative chromatographic elution rates. As the volatile components pass through detector 38, signals will be generated and fed to a suitable recording medium such as a strip chart. The signals can be analyzed by methods known in the art to measure the quantity of volatile components vaporized from the weighed sample.

Periodically it is desirable to heat trap columns 72 and 78 to an elevated temperature over an extended period of time, while sweeping an inert gas therethrough, so as to burn off or volatilize any materials which may have accumulated in these columns. As previously noted, element 147 included in contact pyrometer 145 is an off at limit shorting device which cuts power to heating elements 178 or 179 once trap columns 72 and 78 reach the trap column temperature limit set in contact pyrometer 145. A switch 148 is provided in element 147. When switch 148 is opened, element 147 does not short out. When contact pyrometer 145 is operating in this mode, switch 150 continuously moves between contact points 151 and 152 in response to the temperature of either trap column 72 or 78 as read by thermocouple 180 or 181. When operated in this mode, trap column 72 or 78 is maintained at the preset elevated temperature and the carrier gas fed through the column removes any heavy components which may have been retained in the trap column. After this burn off or flush is completed, switch 148 is returned to its closed position shown in FIG. 5.

Figure 7:
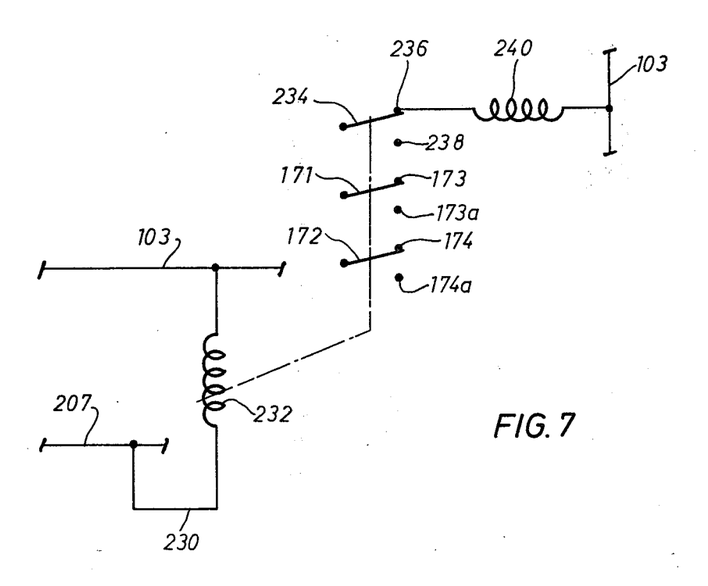
FIG. 7 shows circuits that can be added to the circuits of FIG. 5 to perform certain additional functions.

If desired, the apparatus can be modified so that at the end of a cycle (1) the valve assembly is rotated to its second operating position, and (2) the one trap column heater is cut out of the circuit and the second trap column heater is cut into the circuit. The additional circuits required to perfrom these functions are shown in FIG. 7. When power is fed to line 207, by the closing of switch 220 by the cooling of oven 10, the power flows through line 230 to a stepping relay 232 which throws switches 171, 172, and 234. The throwing of switch 171 from contact point 173 to 173a and switch 172 from contact point 174 to 174a will change the trap column to receive heat in the next cycle. The throwing of switch 234 between contact points 236 and 238 will alternately feed power to an electric solenoid 240. Electric solenoid 240 in turn will control an air solenoid (not shown) which will change the valve assembly from its one operating position to its other by connecting means not shown.

The apparatus of the invention can be employed to measure one or more volatile components present in any type of matrix material whose major components do not vaporize at the maximum temperature employed in the sample heating oven. The apparatus is particularly suitable for analyzing a thermoplastic polymer containing low concentrations of volatile components. It has been established that a 4-alkyl-2,6-ditertiarybutyl phenol such as BHT can be analyzed with an accuracy of ± 1% when present at a level in the range of 100 to 1000 ppm in polyethylene.

What is claimed:

1. Apparatus for chromatographically analyzing volatile components present in a nonvolatile matrix including, in combination:
   (a) An oven,
   (b) A sample cylinder positioned in said oven and including;
      (i) a sealable entry port external of said oven for admitting and withdrawing a sample boat from said cylinder,
      (ii) a gas inlet, and
      (iii) a gas outlet,
   (c) A packed chromatographic analysis column positioned in said oven and including;
      (i) a gas inlet, and
      (ii) a gas outlet,
   (d) A detector downstream of said analysis column,
   (e) A carrier gas line running through said oven,
   (f) First and second packed chromatographic trap columns external of said oven,
   (g) A valve assembly external of said oven;
   (h) Said valve assembly having inlet/outlet connections to;
      (i) the inlet and the outlet of the first trap column,
      (ii) the inlet and the outlet of the second trap column,
      (iii) the carrier gas line,
      (iv) a line connecting to the outlet of the sample cylinder,
      (v) a line connecting to the inlet of the analysis column, and
      (vi) a vent,
   (j) Said valve assembly having two operating positions such that;
      (i) when the valve assembly is in its first operating position, gas introduced into the sample cylinder flows through the first trap column and is vented to the atmosphere, while gas introduced into the gas carrier line flows through the second trap column, the analysis column, and the detector,
(ii) when the valve assembly is in its second operating position, gas introduced into the sample cylinder flows through the second trap column and is vented to the atmosphere, while gas introduced into the gas carrier line flows through the first trap column, the analysis column, and the detector, and
(iii) the direction of gas flow through each of the trap columns is reversed when the valve assembly is rotated from one of its operating positions to its other operating position;
(k) First heating means associated with said oven and including a controller capable of selectively maintaining said oven at a preselected lower temperature and a preselected higher temperature,
(l) Second heating means which maintain the detector at an elevated temperature at least as high as the higher preselected temperature of said oven,
(m) Third heating means which maintain the valve assembly and the lines running therefrom to the oven at a temperature at least as high as the higher preselected temperature of said oven,
(n) Fourth heating means associated with the first trap column and capable of rapidly heating said column to a selected temperature well above the higher preselected temperature of said oven,
(o) Fifth heating means associated with the second trap column and capable of rapidly heating said column to a selected temperature well above the higher preselected temperature of said oven,
(p) Means associated with each of the fourth and fifth heating means for deactivating said heating means when the column reaches its selected temperature,
(q) Switch means which permit only alternate activation of the fourth and fifth heating means,
(r) First control means which activate the first, second, and third heating means, and
(s) Second timed control means which:
(i) at the beginning of its cycle activates the controller of the first heating means so that the oven temperature is heated to and then maintained at its preselected higher temperature,
(ii) at the beginning of its cycle activates the fourth or fifth heating means, and
(iii) at the end of its cycle activates the controller of the first heating means so that the oven temperature is cooled to and then maintained at its preselected lower temperature.

2. Apparatus of claim 1 in which the valve assembly;
(a) Has eight inlet/outlet ports arranged in two series of four each,
(b) Has the inlet/outlet ports in a first fixed valve member with the inlet/outlet ports of each series equidistant from each other and lying in a plane on the circumference of a circle lying in said plane, the radii of said two circles being of different length,
(c) Has a second valve member which seats in gas tight relationship with the first valve member and is rotatable with respect thereto,
(d) Has two fixed operating positions for said second valve member with the second position being reached by rotating said member from its first position through an arc of 90°,
(e) Has means for rotating said second valve member to and from its two fixed operating positions;
(f) Has four arcuate grooves cut in said second valve member, said grooves being arranged in two series of two each such that;
(i) when the valve assembly is in its first operating position, said grooves provide gas passages between two adjacent inlet/outlet ports of the first series, and between two adjacent inlet/outlet ports of the second series,
(ii) when the valve assembly is in its second operating position, said grooves provide gas passages between two adjacent inlet/outlet ports of the first series, and between two adjacent inlet/outlet ports of the second series, and
(iii) each of the inlet/outlet ports is connected to a different inlet/outlet port in (ii) and (iii),
(g) Has the inlet/outlet ports of the first series connected to:
(i) a line connecting to the gas outlet of the sample cylinder,
(ii) one leg of the first trap column,
(iii) one leg of the second trap column, and
(iv) a line connecting to the inlet of the chromatographic analysis column, and
(h) Has the inlet/outlet ports of the second series connected to:
(i) the carrier gas line,
(ii) a line connecting to the inlet of the analysis column,
(iii) one leg of the first rap column, and
(iv) a vent.

3. Apparatus of claim 1 including:
(a) A door on the oven,
(b) Signal-controlled means for opening and closing said door,
(c) Means associated with the timed control means which, at the end of the timed cycle, generate a signal to open the oven door, and
(d) Means associated with the oven which, when the oven falls below its preselected lower temperature, generates a signal to close the oven door.

4. Apparatus of claim 1 including means for rotating the second valve member from one of its operating positions to its other operating position; said means being activated by the beginning of the cycle of the second timed control means.

5. A method for chromatographically analyzing a plurality of samples having volatile components present in a non-volatile matrix by a process carried out in two repetitive, alternating operating cycles, said process consisting essentially of;
in the first cycle;
(a) Introducing a weighed sample into a heating cylinder positioned in an oven heated to a preselected lower temperature,
(b) Increasing the oven temperature to a preselected higher temperature and then maintaining its temperature at said preselected higher temperature for the duration of said cycle.
(c) Introducing a first inert carrier gas into said cylinder at a preselected flow rate;
(d) Feeding said first carrier gas from said cylinder to a first packed chromatographic absorption trap column while maintaining its temperature at least as high as its temperature upon leaving said cylinder,
(e) Passing said carrier gas into and through said first trap column and to the atmosphere while maintaining said trap column at ambient temperature; the direction of gas flow through said trap column being reversed from the direction of flow in the immediately preceding operating cycle, (f) Rapidly heating a second packed chromatographic absorption trap column to a temperature at least as high as the higher preselected temperature of the oven and then terminating said heating, (g) Feeding a second heated carrier gas at a preselected rate into and through said second trap column and to the inlet of a chromatographic analysis column positioned in said oven, the direction of gas flow through said trap column being reversed from the direction of flow in the immediately preceding operating cycle, (h) Feeding the outlet gas of the analysis column to a detector which analyzes said output gas and generates signals indicative of its chemical composition, and (j) Cooling said oven to its lower preselected temperature at the end of the cycle and removing the sample from the sample cylinder, in the second cycle;

(k) Repeating each of steps (a) to (j) with the following modifications:
  (i) heating the first trap column in lieu of the second trap column,
  (ii) maintaining the second trap column at ambient temperature,
  (iii) passing the first carrier gas through the second trap column,
  (iv) passing the second carrier gas through the first trap column.

6. The method of claim 5 in which the samples analyzed are thermoplastic polymers having a volatile additive dispersed therein.

7. The method of claim 6 in which thermoplastic polymer is an ethylene polymer.

8. The method of claim 7 in which the ethylene polymer has a 2,6-ditertiarybutyl-4-alkylphenol dispersed therein.

9. Apparatus of claim 1 in which the sample cylinder:
(a) Is mounted horizontally by passing through the oven wall with a portion thereof extending externally of the oven so that its external terminal end is maintained at substantially ambient temperature at all times,
(b) Has a sealing fixture on its external end providing operator access at all times,
(c) Has its gas inlet external of the oven and near the sealing fixture, and
(d) Is provided with a sample boat which extends throughout a substantial portion of the cylinder's length, said sample boat being provided with a partitioned sample holding zone which is positioned adjacent to the gas outlet of the cylinder.

* * * * *